United States Patent
Takahashi

[11] Patent Number: 5,827,236
[45] Date of Patent: Oct. 27, 1998

[54] INJECTION TOOL AND METHOD OF ITS USE

[75] Inventor: Toyomi Takahashi, Tokyo, Japan

[73] Assignee: Seikagaku Kogyo Kabushiki Kaisha, Tokyo, Japan

[21] Appl. No.: 403,693

[22] PCT Filed: Nov. 10, 1993

[86] PCT No.: PCT/JP93/01638

§ 371 Date: Mar. 13, 1995

§ 102(e) Date: Mar. 13, 1995

[87] PCT Pub. No.: WO94/11042

PCT Pub. Date: May 26, 1994

[30] Foreign Application Priority Data

Nov. 10, 1992  [JP]  Japan ................................. 4-324750
Nov. 10, 1993  [JP]  Japan ................................. 4-324750

[51] Int. Cl.⁶ ............................................. A61M 5/00
[52] U.S. Cl. .......................... 604/240; 604/158; 604/164; 604/165; 604/187; 604/218
[58] Field of Search .................................. 604/117, 158, 604/161, 164, 173, 187, 192, 193, 196–198, 218, 194, 241, 263, 273, 274, 165, 162, 170, 240; 606/108; 128/763

[56] References Cited

U.S. PATENT DOCUMENTS

| | | | |
|---|---|---|---|
| 2,219,605 | 10/1940 | Turkee ........................................ | 128/2 |
| 3,792,703 | 2/1974 | Moorehead ........................... | 128/214.4 |
| 4,013,080 | 3/1977 | Froning .................................... | 128/347 |
| 4,405,307 | 9/1983 | Taylor ...................................... | 604/165 |
| 4,511,356 | 4/1985 | Froning et al. .......................... | 604/164 |
| 4,844,087 | 7/1989 | Garg ........................................ | 128/753 |
| 4,846,799 | 7/1989 | Tanaka et al. ........................... | 604/158 |
| 4,973,312 | 11/1990 | Andrew .................................... | 604/158 |
| 5,026,350 | 6/1991 | Tanaka et al. ........................... | 604/158 |
| 5,147,314 | 9/1992 | Vaillancourt ............................. | 604/158 |

FOREIGN PATENT DOCUMENTS

| | | | |
|---|---|---|---|
| 0221007 | 5/1987 | European Pat. Off. ........ | A61B 10/00 |
| 0169702 | 7/1922 | United Kingdom ................... | 604/273 |

Primary Examiner—Wynn Wood Coggins
Assistant Examiner—Cris L. Rodriguez
Attorney, Agent, or Firm—Sughrue, Mion, Zinn, Macpeak & Seas, PLLC

[57] ABSTRACT

An injection tool that permits a predetermined dose of a drug to be administered accurately at an intended site of a very small size that is located comparatively deep within the body and which develops comparatively high internal pressure, comprises an injection device comprising an injection barrel and an injection needle that is to be mounted at the distal end thereof, a piercing hollow needle having a connector portion connectible to the injection device and a needle portion that allows the injection needle to be inserted therethrough almost tightly, and an inner needle having a basal portion that fits tightly in the of the piercing hollow needle when the connector portion is not connected to the injection device, connector portion and a solid needle portion that is insertable almost tightly in the needle portion, of the piercing hollow needle when the injection needle is not inserted in the needle portion. When using the injection tool, the solid needle portion is inserted in the needle portion of the piercing hollow needle device to be inserted therethrough almost tightly and, at the allowed to pierce to a predetermined site in the body and, subsequently, the inner needle is withdrawn and the injection needle of the injection device is passed through the needle portion while, at the same time, the injection device is connected to the connector portion and, thereafter, a substance to be injected that is held within the injection barrel is injected into the body.

11 Claims, 4 Drawing Sheets

INJECTION TOOL AND METHOD OF ITS USE

TECHNICAL FIELD

This invention relates to an injection tool for administering drugs at sites of a very small size that are located comparatively deep in the body and develop comparatively high internal pressure.

BACKGROUND ART

A known technique for injecting chymopapain for purposes such as the treatment of herniated intervertebral disks in dogs is depicted by rough sketch in FIG. 8 and comprises the following steps: an injection needle 52 that has an inner needle (mandolin) 51 inserted therein is allowed to pierce through the skin 61 and then muscle 62 so that its distal end reaches the vertebral pulp 64 in an intervertebral disk 63 (FIG. 8A); then, the inner needle 51 is withdrawn and a connector 53 at the basal end of the injection needle 52 is filled with part of the drug to be injected; a lure lock 55 at the distal end of the injection barrel 54 into which the drug has been aspirated is coupled to the connector 53; and the piston 56 is pushed, thereby injecting the drug into the vertebral pulp 64 (FIG. 8B) (see "Kachiku Chiryo (Domestic Treatment)", No. 1, Treatment of Herniated Intervertebral Disks in Dogs by Chymopapain Injection, compiled under the supervision of Masashige Nakayama, published by Inters Videotape Co., Ltd., 1992).

Stated more specifically, the vertebral pulp 64 in the intervertebral disk 63 is a closed space surrounded with a fibrous ring 66 and is located at a comparatively deep site in the body; hence, in order to assure penetration through the skin 61, muscle 62 and even the fibrous ring 66, the injection needle 52 must have a reasonable thickness and, at the same time, it is necessary to use the inner needle 51 so that the injection needle 52 will neither bend nor undergo obstruction by tissue fragments during piercing.

To this end, the injection needle 52 is a separate member from the injection barrel 54 in the current method and when the needle tip has reached the intended site, the inner needle 51 is withdrawn and the injection barrel 54 is connected. However, with the current means of coupling the lure lock 55 to the drug filled connector 53, it is impossible to avoid inaccuracy in the injected dose of the drug. What is more, complete exclusion of air is difficult to achieve by the means of connecting the injection barrel after the connector 53 is filled with the drug and any residual air will cause further inaccuracy in the injected dose of the drug.

In addition, when the injection needle 52 is pulled out after injection, a considerably large piercing hole remains in the fibrous ring 66 due to the injection needle 52, and the drug that has been injected into the vertebral pulp 64, developing high internal pressure, is prone to flow out of the piercing hole, thus introducing inaccuracy in the drug dosage and also damaging the surrounding tissue by the drug outflow.

Therefore, even if one attempts to employ the aforementioned technique for administering drugs at sites of a very small size that are located comparatively deep in the body and develop comparatively high internal pressure not only in the treatment of herniated intervertebral disks in dogs but also in the treatment of similar diseases such as herniated intervertebral disks in humans, difficulty is involved in accurately administering predetermined doses and, at the same time, a considerably large piercing hole remains, requiring a long time for it to close, during which time not only the drug but also blood and other body fluids can potentially flow out in large quantities.

The problem to be solved by the present invention is that there has not been available any injection-based drug administering means by which predetermined doses of drugs can be administered in an accurate manner at sites of a very small size that are located comparatively deep in the body and develop comparatively high internal pressure, and which yet will not leave a large piercing hole open at the intended site.

DISCLOSURE OF INVENTION

The present invention provides (1) an injection tool comprising an injection device comprising an injection barrel and an injection needle that is to be mounted at the distal end thereof, a piercing hollow needle having a connector portion that is to be connected to the aforementioned injection device and a needle portion that allows the aforementioned injection needle to be inserted almost tightly, and an inner needle having a basal portion that is to be fitted tightly in the aforementioned connector portion and a solid needle portion that is to be inserted almost tightly in the aforementioned needle portion, and (2) a method of using an injection tool characterized in that a solid needle is inserted almost tightly in the needle portion of a piercing hollow needle having a connector portion that is to be connected to an injection device comprising an injection barrel and an injection needle mounted at the distal end thereof and said needle portion that enables the injection needle of the aforementioned injection device to be inserted therethrough almost tightly and, at the same time, the aforementioned needle portion is allowed pierce to a predetermined site in the body of interest with an inner needle having said solid needle fixed in said piercing hollow needle and, subsequently, said inner needle is withdrawn and the injection needle of the aforementioned injection device is passed through said needle portion while, at the same time, the aforementioned injection device is connected to the aforementioned connector portion and, thereafter, the substance to be injected that is held within the aforementioned injection barrel is injected into said body of interest. This invention solves the aforementioned problems, permitting a predetermined dose of a drug to be administered in an accurate manner at a site of a very small size that is located comparatively deep in the body and comparatively high internal pressure without causing a large piercing hole to open at the intended site.

The injection tool of the present invention comprises an injection device, a piercing hollow needle and an inner needle, with its basic structure being such as to permit injection of drugs and the like by a conventional method of injection, and is characterized in that a mechanism that establishes connection between the piercing hollow needle and the connector portion is provided on the injection device, which mechanism allows the position of the tip of the injection needle to be restricted by the needle portion of the piercing hollow needle so as to ensure easy and accurate injection. Further, the piercing hollow needle which is comparatively thick and rugged and which has the solid needle inserted for reinforcement and for closing the hollow portion is preliminarily forced to reach the neighborhood of the intended site and, thereafter, the injection needle of the injection device is inserted through the interior of said hollow needle; hence, even if said injection needle used is comparatively thin and has low strength, it can be allowed to reach the intended site in an accurate manner without bending. What is more, the use of such injection tool of the present invention enables the use of an injection device such as a microsyring that comprises a thin injection needle and barrel, with the result that a small dose of a drug can be injected at a site of a very small size without any resistance and in an accurate manner.

A preferred structure of the injection device of the present invention is such that an end portion of the injection needle is provided with a member that fits in said connector portion (which is hereunder referred to as a needle base) and that a connecting piece that holds said needle base tightly and which establishes communication between the injection needle and the injection barrel is provided as said connecting means. Said needle base has a mechanism that permits it to be held in the piercing hollow needle and it also has the ability to allow the position of the tip of the injection needle to be restricted by the needle portion of the piercing hollow needle so as to ensure easy and accurate injection. Furthermore, said needle base may be adapted to be movable along the connecting piece parallel to the longitudinal direction of the injection needle and this is preferred since it offers the additional advantage of contributing to fine adjustment of the position of the tip of the injection needle. In this case, a graduation may be provided that indicates the amount of movement.

The injection needle and the needle base may be separate members or they may be integrated in a unitary member. Further, the connecting piece may be rendered integral with the injection barrel.

In the present invention, the needle portion of the piercing hollow needle has preferably such a length that when the basal portion of the inner needle is fitted in the aforementioned connector portion, the distal end aligns with that of the aforementioned solid needle and that when the aforementioned needle device is connected to the aforementioned connector portion, the distal end portion of the aforementioned injection needle will project from the distal end.

To implement the method of the present invention, the inner needle is inserted into the piercing hollow needle and the basal portion of said inner needle is fitted to be fixed in the connector portion of said hollow needle, which is then allowed to pierce into the body with the solid needle of said inner needle being mounted in the needle portion of said hollow needle and, preferably, the inner needle is withdrawn when the distal end has reached close to the intended site. When a drug or the like is injected in the next step, the injection needle is inserted through the needle portion of said hollow needle so that the injection device is coupled to the connector portion of said hollow needle and the distal end of the injection needle is preferably allowed to project beyond the needle portion of said hollow needle by a predetermined amount in order to have said distal end reach the intended site. This is because when injecting a drug to an intended site such as vertebral pulp that has high internal pressure, one only need allow the needle portion of the piercing hollow needle to reach the outer side of the fibrous ring surrounding that vertebral pulp and then the drug can be injected into the vertebral pulp leaving only a very small piercing hole in the neighborhood of the intended site that forms on account of the injection needle which has substantially the same diameter as the inside diameter of the needle portion of the piercing hollow needle.

KEY TO SYMBOLS

Figure 1A:
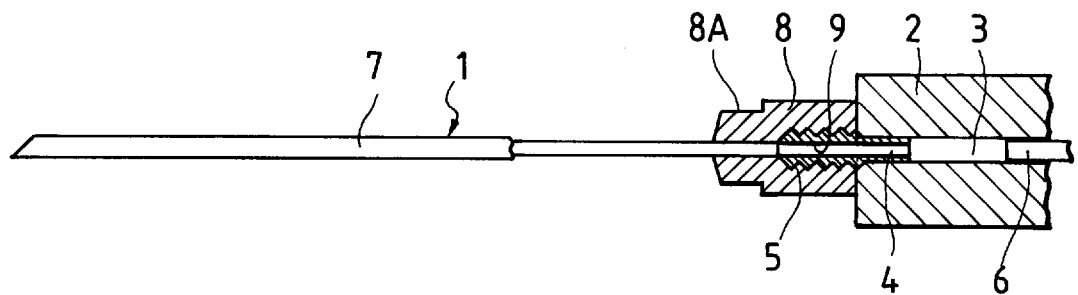
FIG. 1 is a longitudinal section showing an example of the present invention, with FIG. 1A showing the injection device, FIG. 1B showing the piercing hollow needle and FIG. 1C showing the inner needle.

1: Injection device
2: Injection barrel
7: Injection needle
8: Needle base
11: Piercing hollow needle
12: Connector portion
13: Needle portion
21: Inner needle
22: Basal portion
25: Solid needle

BEST MODE FOR CARRYING OUT THE INVENTION

An embodiment of the present invention will now be described with reference to the drawings. Referring to FIG. 1A, injection device 1 comprises an injection barrel 2 that has a small-diameter cylinder compartment 3 formed through it on the central longitudinal axis and which has the basal end portion of a short tubular connecting piece 4 fitted into and fixed at the distal end of the cylinder compartment 3; the connecting piece 4 has the same outside diameter as the diameter of the cylinder compartment 3 and it also has a mounting thread portion 5 in the distal end portion; further, a plunger 6 is fitted into the cylinder compartment 3 from the basal end. Needle base 8 of an injection needle 7 has an inner thread portion 9 that fits threadably over the mounting thread portion 5, whereby the injection needle 7 is mounted at the distal end of the injection barrel 2.

Thus, the injection needle 7 can be attached or detached from the injection barrel 2 so that one may use a suitable type that is selected from a stock of various types having different lengths and diameters.

Figure 1B:
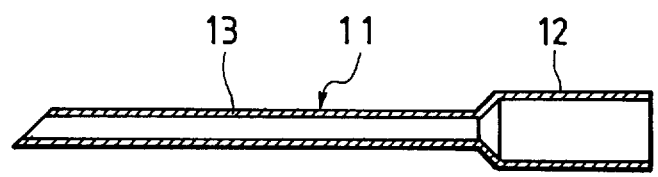

Referring to FIG. 1B, piercing hollow needle 11 has in unitary assembly a cylindrical connector portion 12 that has an inside diameter small enough to permit tight fitting of a small-diameter portion 8A at the distal end of the needle base 8 and which is adequately longer than the small-diameter portion 8A, as well as a needle portion 13 that extends forward from the distal end of the connector portion 12, that has an inside diameter slightly larger than the outside diameter of the injection needle 7 and that has such a length that the distal end portion of the injection needle 7 will project from the distal end by a predetermined length.

Given the same intended site at which a drug is to be administered, the depth from the skin surface to the intended site and the hardness of the tissue reaching that site will vary differently depending upon the physical constitution of each individual and, hence, the needle portion 13 is designed to have an adequate length in consideration of maximum depth, and in order to prevent the occurrence of bending or obstruction by a tissue fragment during piercing, the needle portion 13 is fitted with an inner needle 21 to be described later.

Figure 1C:
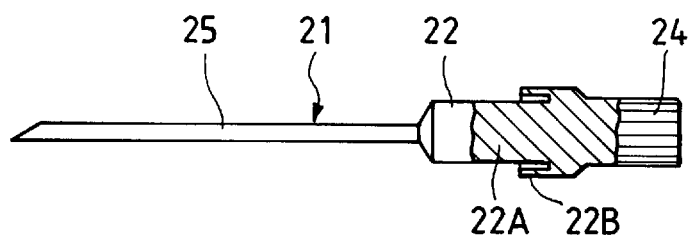

Referring to FIG. 1C, the inner needle 21 has in unitary assembly a basal portion 22 consisting of a cylindrical fit-in portion 22A that is to be fitted deep and tightly into the middle part of the connector portion 12 of the piercing hollow needle 11 and an annular hugging portion 22B that is located outside said fit-in portion 22A and which is to make intimate contact with the outer circumference of the basal portion of the connector portion 12, as well as a knob 24 formed at the basal end of the basal portion 22, and a solid needle 25 that extends forward from the distal end of the fit-in portion 22A, that has an outside diameter slightly smaller than the inside diameter of the needle portion 13 and which has such a length that its distal end will align with that of the needle portion 13.

Figure 2:
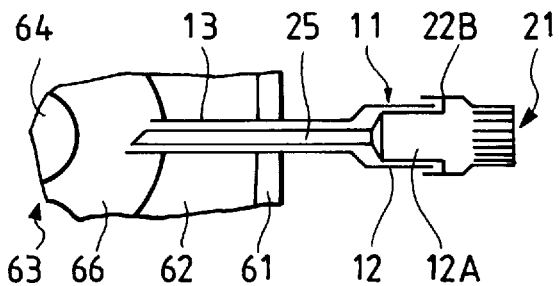
FIG. 2 is a section showing the piercing hollow needle as it has pierced into the body.

The example under consideration which has the structure described above may be used to administer a drug for the treatment of herniated intervertebral disks, such as chymopapain, collagenase or chondroitin, and this use will now be described with reference to FIG. 2 and the drawings that follow.

First, the inner needle 21 is inserted into the piercing hollow needle 11 from the connector portion 12 and fixed as the fit-in portion 22 is fitted in the connector portion 12 and the hugging portion 22B is placed in intimate contact with its periphery. In this case, the solid needle 25 is inserted into the needle portion 13 almost tightly and their distal ends will align with each other but it is also necessary to insure that the inclinations of the oblique needle tips are not staggered but aligned. To this end, it is preferred that a projection is provided, for example, on the outer circumference of the basal end of the connector portion 12 while, at the same time, a cutout is provided at the distal end of the hugging portion 22B (both the projection and the cutout are not shown), with them being brought into mutual engagement, thereby establishing an in-phase relationship to assure directional alignment between those inclinations. The piercing hollow needle 11 having the inner needle 21 thus fitted therein is allowed to penetrate the skin 61 and the muscle 62 until its distal end reaches the outer portion of the fibrous ring 66 of an intervertebral disk 63 (see FIG. 2).

It should be mentioned here that the piercing hollow needle 11 and the inner needle 21 are sometimes supplied in a coupled state by manufacturers of injection tools and, in that case, they are allowed to pierce into the body as such.

Figure 3:
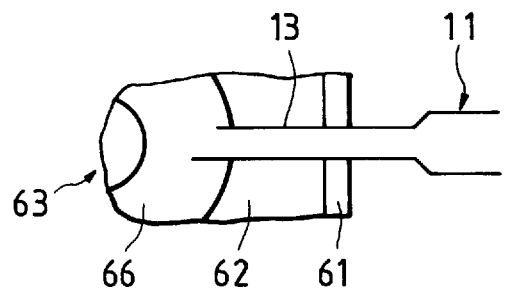
FIG. 3 is a section equivalent to FIG. 2 except that the inner needle has been withdrawn.

In the next step, the piercing hollow needle 11 is fixed by holding the connector portion 12 with the fingertips so that it will not move and, then, the knob 24 is pulled to withdraw the inner needle 21 (see FIG. 3).

Figure 4:
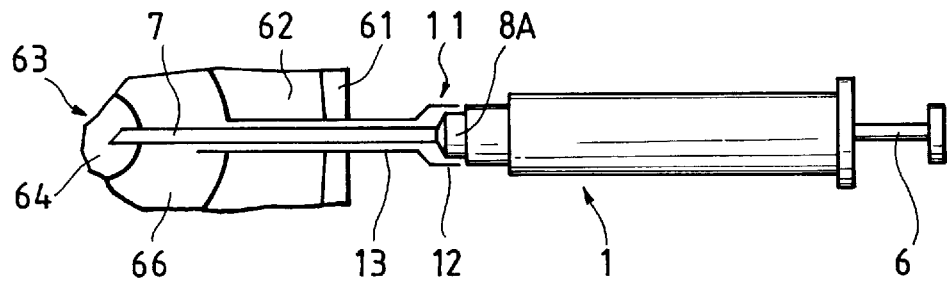
FIG. 4 is a section showing the injection device as it is coupled to the piercing hollow needle for drug injection.

With the piercing hollow needle 11 thus inserted in the body, the injection needle 7 of the injection device 1 that has had a drug aspirated into the cylinder compartment 3 is inserted through the needle portion 13 from the connector portion 12 and its distal end is allowed to project beyond the needle portion 13 so that it will penetrate the fibrous ring 66 to reach the vertebral pulp 64 at the intended site. In this case, the small-diameter portion 8A at the distal end of the needle base 8 is fitted tightly into the basal portion of the connector portion 12 so that the injection device 1 becomes coupled to the piercing hollow needle 11 (see FIG. 4). Then, the plunger 6 is pushed so that a predetermined dose of the drug in the cylinder compartment 3 is injected via the injection needle 7 into the vertebral pulp 64 and when the injection ends, the injection device 1 and the piercing hollow needle 11 are withdrawn either together or separately.

It should also be mentioned that since the injection needle 7 of the injection device 1 which is illustrated as an example in FIG. 1A has an extremely fine inside diameter, it is difficult to aspirate a viscous drug via the injection needle 7 for drug aspiration into the cylinder compartment 3. In a case such as this, one may use a drug aspirating hollow needle having a larger inside diameter than the injection needle 7, connect it to the injection barrel 2, aspirate the drug into the cylinder compartment 3 and thereafter replace said hollow needle with the injection needle 7.

When administering the drug, the distal end of the injection needle 7 must be allowed to reach the vertebral pulp 64 as its distal end is permitted to project from that of the needle portion 13 of the piercing hollow needle 11 by a predetermined length in an accurate manner. To this end, a graduation having a cardinal point in the position where the distance from the distal end of the injection needle 7 is equal to the length of the piercing hollow needle 11 may preferably be provided along the length of the needle base 8 starting at the basal end portion of the injection needle 7 (see FIG. 5) so as to ensure projection by a predetermined length by reading the numeral on the scale that enters the connector portion 12. Alternatively, a mark may be provided in the position of said cardinal point on the injection needle 7 and the distance of movement of this mark relative to a graduation provided on a transparent connector portion 12 is read, thereby allowing projection by a predetermined length; this is also a preferred embodiment.

In the example under consideration, a microsyringe in which the cylinder compartment 3 does not have a much greater diameter than the injection needle 7, so that it is suitable for micro-injection, is used as the injection device 1, and due to the small drug resistance that develops in the cylinder compartment 3, only a small force is required to push the plunger 6. Further, the absence of the need to fill the connector portion with a drug as in the prior art and the very small dose of the drug that is injected per unit stroke length of the plunger 6 and, further, the injection of the drug through the injection needle 7 which is preliminarily mounted on the injection barrel 2, combine together to permit injection of a predetermined dose in an accurate manner.

Further, in the example under consideration, the connector portion 12 is designed to be long enough compared to the length of the needle base 8 to which it is fitted so that blood or other body fluids will not immediately spread to the surrounding area even if they should flow out through the needle portion 13; in addition, the resistance or backset that would otherwise occur due to the compression of filled air when the needle base 8 is tightly fitted in the connector portion 12 is practically absent, assuring high stability when coupling the injection device 1 to the piercing hollow needle 11.

It should be noted that the injection barrel 2 may be coupled to the connector portion 12 by a lure lock mechanism whereas the inner needle 21 may be coupled to the piercing hollow needle 11 by merely slipping the hugging portion 22B over the connector portion 12.

It should also be noted that while the foregoing description concerns the case of using the example in the administration of a drug for the treatment of a herniated intervertebral disk, the use of the injection tool of the present invention is by no means limited to intervertebral disks but it can be used appropriately at any site of a very small size such as eyeballs that are located comparatively deep in the body and develop comparatively high internal pressure.

A specific embodiment of each of the mechanism for aligning the tip of the piercing hollow needle with that of the solid needle of the inner needle or the injection needle and the mechanism for adjusting the length by which the injection needle is to project from said hollow needle of the injection needle will now be described with reference to FIGS. 5 to 7.

Figure 5:
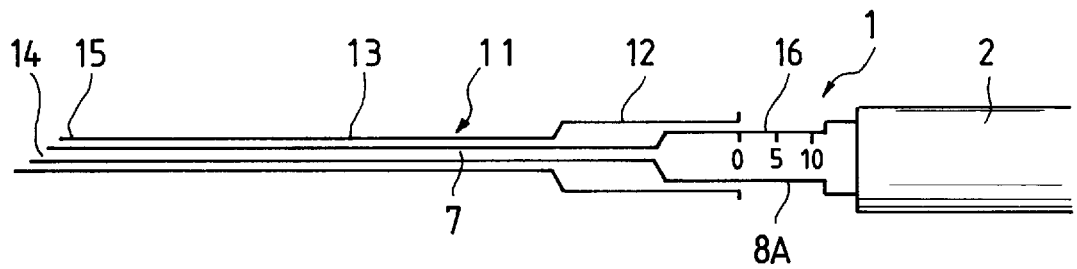
FIGS. 5, 6 and 7 are diagrams illustrating two mechanisms for use in the present invention, one for aligning the tip of the piercing hollow needle with that of the solid needle of the inner needle or the injection needle, and the other for adjusting the length by which the injection needle is to project from said hollow needle, with FIG. 5 being a sectional view, FIG. 6 a perspective view of the essential part and FIG. 7 showing another embodiment of the mechanism shown in FIG. 6.

FIG. 5 is a sectional view showing the injection needle 1 that has a graduation 16 provided in the small-diameter portion 8A at the needle base and which has the injection needle tip 14 align with the needle portion's tip 15 of the piercing hollow needle by reference to numeral zero on the scale; FIG. 6 is a perspective view of the essential part which illustrates the relationship of coupling between the connector portion 12 of the piercing hollow needle 11 and the small-diameter portion 8A at the needle base of the injection device 1.

Said small-diameter portion 8A at the needle base is provided with not only the graduation 16 but also a groove 17 for withdrawing air from the connector portion, as well as a ridge 18, whereas the connector portion 12 of the piercing hollow needle 11 is provided with a recess 19 that fits tightly with said ridge. Therefore, one only need fit said ridge 18 in the recess 19 to assure that the directions of openings in the respective needle tips are in alignment as shown in FIG. 5 and, at the same time, the tip of the injection needle can be allowed to project beyond the needle portion 13 by a desired length by using the graduation 16 as an index.

The provision of the groove 17 in said small-diameter portion at the needle base offers the added advantage of permitting smooth movement of the needle tip.

The groove 17 may be replaced by a plurality of recesses that are provided in the connector portion 12 of the piercing hollow needle. Such an embodiment is shown in FIG. 7A or 7B, 7A showing the case of providing two recesses and 7B four recesses. The small-diameter portion 8A at the needle base does not have the groove 17 shown in FIG. 6 but is provided with one ridge 18; a register mark 20 for positioning the injection needle tip is provided in the connector portion.

With a plurality of recesses provided in the connector portion 12 of the piercing hollow needle, the degassing groove 17 in the needle base can be eliminated and, at the same time, the tip of the piercing hollow needle and that of the injection needle can be set in a desired relationship. In the case where the distal end of the injection needle is provided with a lateral hole, a desired position of the opening can be selected, thereby permitting the selection of an effective direction for drug ejection.

While the provision of the ridge 18 on the small-diameter portion 8A at the needle base and the recess 19 in the connector portion 12 has been described above as a registration mechanism, this is not the only possible registration mechanism, and other embodiments of the invention having the same capability may also be adopted. For example, one or more recesses may be provided in the small-diameter portion 8A at the needle base with a ridge that fits in this recess is provided on the connector portion.

Figure 6:
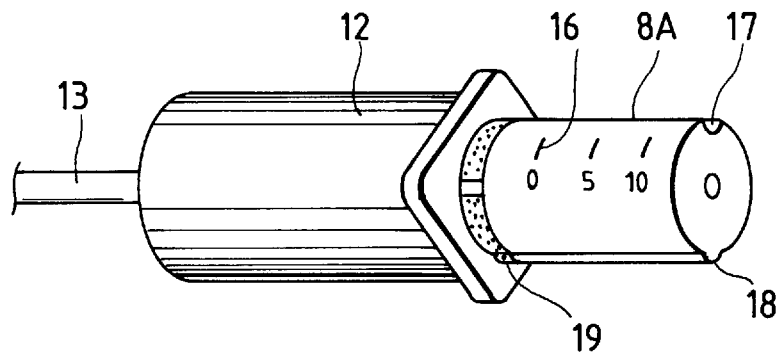
Figure 7A:
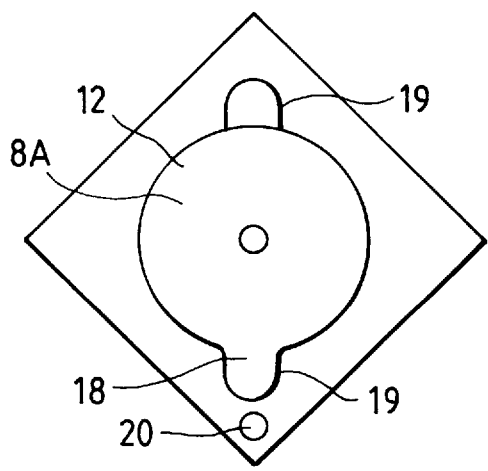
Figure 7B:
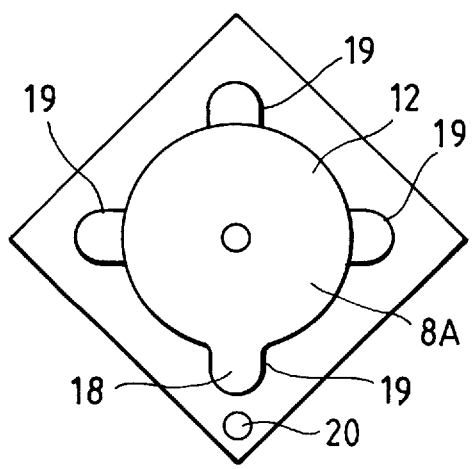
Figure 8A:
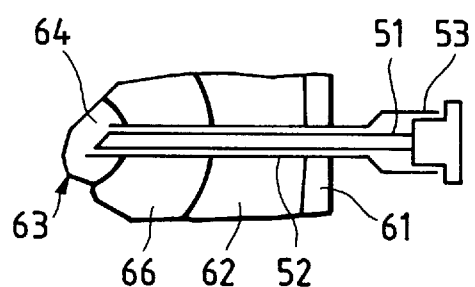
FIGS. 8A and 8B are rough sketches in section that illustrate a prior art technique for drug injection.
Figure 8B:
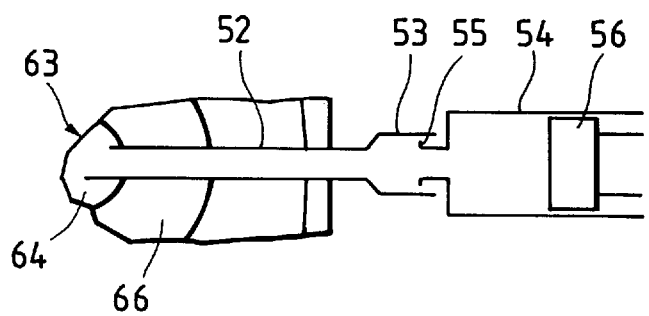

The mechanism that is shown in FIGS. 6 and 7 which fits the connector portion 12 of the piercing hollow needle to the small-diameter portion 8A at the needle base of the injection device may be applied to the mechanism for fitting said connector portion 12 to the basal portion 22 of the inner needle 21. More specifically, groove 17 and ridge 18, provided on said small-diameter portion 8A at the needle base, may be provided in the basal portion 22 of the inner needle so that the tip of the solid needle 25 of the inner needle can be easily aligned with the tip 15 of the piercing hollow needle.

According to the present invention, the injection needle is inserted through the needle portion of the piercing hollow needle as it is guided and protected by the latter and its distal end portion is allowed to project beyond the latter so that it reaches the intended site; therefore, by permitting the distal end of the needle portion to reach close to the intended site, one only need allow the injection needle to project by a small amount; hence, the intended site can be reached by piercing even through a deep or hard tissue without potential hazards such as bending, and the drug in the injection barrel can be injected at the intended site of a very small size by a predetermined dose in an accurate manner.

As a further advantage, the piercing hole that remains open at the intended site is the diameter of the injection needle and, hence, even at a high internal pressure, the outflow of the drug is extremely small and, in addition, due to the rapid closing of that small hole, the outflow of blood and other body fluids is small.

I claim:

1. An injection tool comprising:
   an injection device comprising an engagement device, an injection barrel having a distal ends and an injection needle mounted at said distal end;
   a piercing hollow needle having a connector portion with a corresponding engagement device for connecting said piercing hollow needle to said injection device and a needle portion that allows said injection needle to be inserted therethrough almost tightly, wherein, upon connecting said connector portion of said piercing hollow needle to said injection device, said engagement device engages with said corresponding engagement device to provide a non-rotating reciprocal relationship therebetween such that said injection needle of said injection device is translatable and non-rotatable within said needle portion of said piercing hollow needle; and
   an inner needle having a basal portion tightly fittable into said connector portion of said piercing hollow needle when said connector portion is not connected to said injection device and a solid needle portion, for reinforcing said needle portion of said piercing hollow needle, insertable almost tightly in said needle portion of said piercing hollow needle when said injection needle is not inserted in said needle portion.

2. An injection tool as recited in claim 1, wherein said injection device is provided with a member that fits in said connector portion and receives an end portion of said injection needle, and a connecting piece that connects said injection needle to said injection barrel and which holds said member tightly, and said engagement device being provided on said member.

3. An injection tool as recited in claim 1, wherein said needle portion of said piercing hollow needle has a length such that when said basal portion of said inner needle is fitted in said connector portion, a distal end of said needle portion aligns with a distal end of said solid needle portion of said inner needle, and when said injection device is connected to said connector portion, a distal end portion of said injection needle projects from said distal end of said needle portion.

4. An injection tool as recited in claim 1, wherein said engagement device is a longitudinal groove and said corresponding engagement device is a longitudinal ridge.

5. An injection tool as recited in claim 1, wherein said engagement device is a longitudinal ridge and said corresponding engagement device is a longitudinal groove.

6. An injection tool comprising an injection device, a piercing hollow needle and an inner needle, wherein said injection device 1 comprises an injection barrel 2 having a distal end and an injection needle 7 mounted at said distal end of said injection device 1 and having a needle base 8 with a distal end portion provided with an engagement device;

said piercing hollow needle comprises a connector portion 12 and a needle portion 13, said connector portion 12 having a corresponding engagement device and configured to have said distal end portion of said needle base 8 of said injection needle 7 fittable therein such that said engagement device engages with said corresponding engagement device, and said needle portion 13 being capable of insertion through said injection needle 7 almost tightly and having a length such that when said needle base 8 is fitted in said connector portion 12, a distal end portion of said injection needle 7 projects from a distal end of said needle portion 13, wherein upon fitting said distal end portion of said needle base into said connector portion of said piercing hollow needle, said engagement device engages with said corresponding engagement device to provide a non-rotating reciprocal relationship therebetween such that said injection needle of said injection device is translatable and non-rotatable within said needle portion of said piercing hollow needle; and said inner needle comprises a basal portion 22 and a solid needle portion 25 for reinforcing said needle portion 13, said basal portion 22 tightly fittable in said connector portion 12, and said solid needle portion 25 insertable in said needle portion 13 almost tightly and having a length such that when said basal portion 22 is fitted in said connector portion 12, a distal end of said solid needle portion 25 will align with that of said needle portion 13.

7. An injection tool as recited in claim 6, wherein said engagement device is a longitudinal groove and said corresponding engagement device is a longitudinal ridge.

8. An injection tool as recited in claim 6, wherein said engagement device is a longitudinal ridge and said corresponding engagement device is a longitudinal groove.

9. A method for using an injection tool comprising the steps of:

inserting an inner needle almost tightly in a piercing hollow needle for reinforcing said piercing hollow needle, said piercing hollow needle having an engagement device;

piercing a body with said piercing hollow needle to a predetermined site in said body;

withdrawing said inner needle from said piercing hollow needle;

inserting an injection device having an injection barrel, a corresponding engagement device, and an injection needle into said piercing hollow needle, such that said engagement device engages with said corresponding engagement device to provide a non-rotating reciprocal relationship therebetween such that said injection needle of said injection device is translatable and non-rotatable within said piercing hollow needle ; and injecting a substance held in said injection barrel into said body through said injection needle.

10. A method for using an injection tool according to claim 9, further comprising the step of forming said piercing hollow needle by providing a connector portion for fixing said injection device to said piercing hollow needle and for fixing said inner needle to said piercing hollow needle when said injection device is not connected to said piercing hollow needle.

11. A method for using an injection tool according to claim 9, further comprising the step of forming said inner needle by providing a solid needle portion for insertion into said hollow piercing needle.

* * * * *